United States Patent [19]

Bugglin et al.

[11] Patent Number: 5,210,192
[45] Date of Patent: May 11, 1993

[54] PROCESS FOR THE PREPARATION OF 3,7-DIALKYLXANTHINES

[75] Inventors: Marius Bugglin; Herbert Gropp, both of Minden; Lothar Janitschke, Kleinniedesheim; Ulrich Karl, Weinheim; Hans-Heinrich Lenz, Minden, all of Fed. Rep. of Germany

[73] Assignee: BASF Aktiengesellschaft, Ludwigshafen, Fed. Rep. of Germany

[21] Appl. No.: 835,455
[22] PCT Filed: Sep. 4, 1990
[86] PCT No.: PCT/EP90/01478
 § 371 Date: Mar. 2, 1992
 § 102(e) Date: Mar. 2, 1992
[87] PCT Pub. No.: WO91/03477
 PCT Pub. Date: Mar. 21, 1991

[30] Foreign Application Priority Data

Sep. 6, 1989 [DE] Fed. Rep. of Germany ....... 3929589

[51] Int. Cl.$^5$ ............................................. C07D 473/10
[52] U.S. Cl. ..................................... 544/273; 544/267
[58] Field of Search ............... 544/273, 266, 267, 262; 514/262, 263

[56] References Cited
PUBLICATIONS

Berichte Der Deutschen Chemischen Gesellschaft, Verlag Chemie 1982-pp. 1409-1422, H. Biltz et al. vol. 61.
H. Biltz et al., Chem Ber. 1931, vol. 64, p. 1970.

Primary Examiner—Nicholas S. Rizzo
Attorney, Agent, or Firm—Keil & Weinkauf

[57] ABSTRACT

The invention is directed to a process for preparing 3,7-dialkylxanthines of the formula I

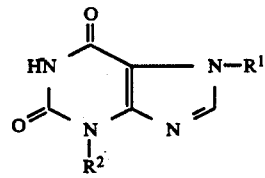

($R^1$ and $R^2$ denote $C_1$-$C_4$-alkyl) by the reaction of 4-amino-imidazolecarboxamide-(5) of the formula II

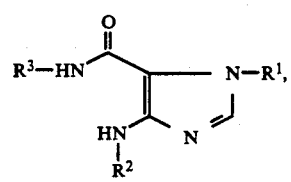

with an alkali cyanate in aqueous solution at a pH of from 3 to 5 followed by cyclization of the resulting urea derivative at a pH of from 8 to 14.

1 Claim, No Drawings

PROCESS FOR THE PREPARATION OF 3,7-DIALKYLXANTHINES

DESCRIPTION

The present invention relates to a novel process for the preparation of 3,7-dialkylxanthines of the general formula I

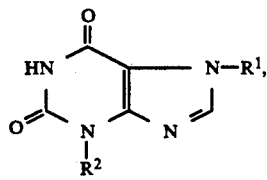

in which $R^1$ and $R^2$ denote $C_1$–$C_4$-alkyl.

Hitherto, 3,7-dialkylxanthines have only been obtainable by expensive total synthese or by isolation from vegetable products such as cocoa beans or tea waste products. An exception is the partial snythesis of theobromine (3,7-dimethylxanthine) proposed by H. Biltz et al., [Chem. Ber. (1931), Vol. 64, page 1970], in which hydrogen chloride is passed, at 160° C., through a melt of caffeidine and methyl or ethyl urea. This process suffers from the drawbacks that the highly corrosive melt is difficult to handle and purification of the theobromine is an expensive procedure. A further disclosure from the work of H. Biltz et al., [Chem. Ber. (1928). Vol. 61, 1409] is the reaction of caffeidine with potassium cyanate in aqueous solution to produce caffeine. According to the experimental data, this reaction takes place in a weakly acid to neutral medium at a pH of from 5.5 to 7.5.

It is an object of the present invention to provide novel processes for the preparation of 3,7-dialkylxanthines.

Accordingly, we have found a process for the preparation of 3,7-dialkylxanthines of the general formula I

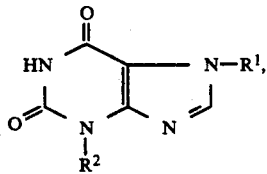

in which $R^1$ and $R^2$ denote $C_1$–$C_4$-alkyl, wherein a 1-alkyl-4-alkylamino-5-alkylaminocarbonylimidazole of the general formula II

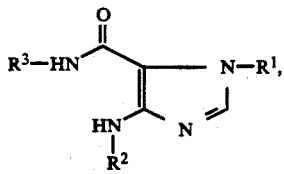

in which $R^3$ denotes $C_1$–$C_4$-alkyl, is reacted with an alkali metal cyanate in aqueous solution at a pH of from 3 to 5, and the resulting urea derivative is subjected to cyclization at a pH of from 8 to 14 to form the corresponding 3,7-dialkylxanthines (I).

The fact that this reaction effects cleavage of the amine $R^3$—$NH_2$ must, in view of the paper by H. Blitz et al. on caffeine synthesis (loc. cit.), be regarded as a surprising feature.

The starting materials II, of which caffeidine ($R^1$, $R^2$ and $R^3$ denote methyl) is the most significant, are known or can be prepared by known methods. They are preferably prepared by alkaline hydrolysis of the corresponding 1,3,7-trialkylxanthines III

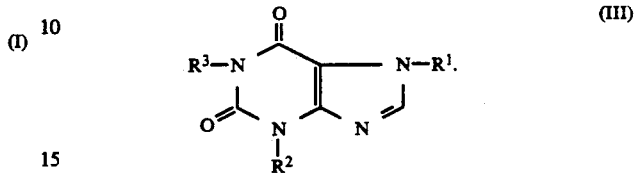

Other important starting materials are those in which $R^1$ and $R^2$ denote ethyl or isopropyl groups.

In the process of the invention, the aqueous solutions of the compounds II are adjusted to a pH of from 3 to 5 with an acid.

Examples of suitable acids are mineral acids such as hydrochloric acid, sulfuric acid and phosphoric acid, or organic acids such as acetic acid, formic acid and oxalic acid, and since the reaction is pH-sensitive, buffer systems may be used to maintain specific pH's, examples being sodium acetate/acetic acid or sodium dihydrogen phosphate/disodium hydrogen phosphate.

In the preparation of theobromine, yields of more than 60% are obtained in a pH range of from 4.3 to 4.7. When using a caffeidine homologue as starting material, the optimum pH range can be readily determined by carrying out preliminary tests.

Preferredalkali metal cyanates are sodium cyanate and potassium cyanate used in a concentration of from 1 to 4 moles and preferably from 1 to 2 moles, per mole of II. A greater excess of alkali metal cyantate is possible, but not necessary. The concentration of compound II in the aqueous solution is not critical and is usually in the range of from 0.2 to 4 moles per liter. When preparing theobromine, the best results are obtained at a caffeidine concentration of from 0.5 to 2 moles per liter. The reaction proceeds satisfactorily at from 0° to 50° C. The use of higher temperatures is possible, but this leads to an increased consumption of alkali metal cyanate.

The resulting urea derivative IV

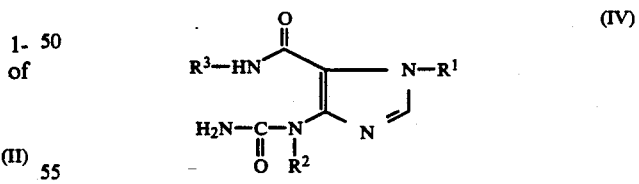

can be isolated or converted to 3,7-dialkylxanthines in situ. Cyclization to compounds I is effected in an alkaline medium at elevated temperature. A pH ranging from 11 to 13 is particularly preferred, whilst a value of from 11.6 to 12.0 is to be partically recommended for the preparation of theobromine.

The 3,7-dialkylxanthines can be isolated by adjusting the pH to the isoelectric point to effect precipitation, followed by filtration and extraction with a suitable solvent. The end products, particularly theobromine and its derivatives, are known to be pharmacological agents of considerable importance.

EXAMPLE

A solution of 84 g (0.5 mole) of caffeidine in 450 ml of water was adjusted to pH 4.5 with glacial acetic acid, and 41.6 g (0.66 mole) of sodium cyanate were added portionwise thereto over a period of 4.5 hours at 25° C. After standing for 12 hours, the precipitated solids were redissolved in 100 ml of water, and the solution was adjusted to pH 11.8 with 100 ml of a 50% caustic soda solution. The reaction solution was then heated at the boil for 1.5 hours.

The product was isolated by adjusting the solution to pH 6.1 with glacial acetic acid. Theobromine precipitated on cooling. The theobromine was filtered off, washed with water and a little acetone and once again with hot water.

Yield: 62.8% M.p. 350° C.

We claim:

1. A process for the preparation of a 3,7-dialkylxanthine of the formula I

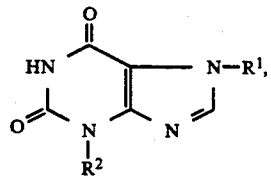

in which $R^1$ and $R^2$ denote $C_1$–$C_4$-alkyl, wherein a 1-alkyl-4-alkylamino-5-alkylaminocarbonylimidazole of the formula II

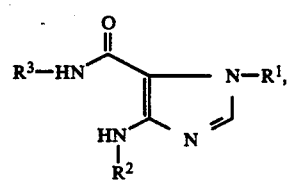

in which $R^3$ denotes $C_1$–$C_4$-alkyl, is reacted with an alkali metal cyanate in aqueous solution at a pH of from 3 to 5, and the resulting urea derivative is subjected to cyclization at a pH of from 8 to 14 to form the corresponding 3,7-dialkylxanthine (I).

* * * * *